US00PP37693P2

(12) United States Plant Patent
Huber

(10) Patent No.: US PP37,693 P2
(45) Date of Patent: Sep. 15, 2026

(54) ***DAHLIA* PLANT NAMED 'LeeAnn's FD168D'**

(50) Latin Name: *Dahlia hybrida*
Varietal Denomination: LeeAnn's FD168D

(71) Applicant: Coseytown Flowers LLC, State Line, PA (US)

(72) Inventor: LeeAnn Huber, Greencastle, PA (US)

(73) Assignee: Coseytown Flowers llc, State Line, PA (US)

( * ) Notice: Subject to any disclaimer, the term of this patent is extended or adjusted under 35 U.S.C. 154(b) by 0 days.

(21) Appl. No.: 19/406,877

(22) Filed: Dec. 2, 2025

(51) Int. Cl.
*A01H 5/02* (2018.01)

(52) U.S. Cl.
USPC ..... Plt./321

(58) Field of Classification Search
USPC ..... Plt./321
See application file for complete search history.

(56) References Cited

U.S. PATENT DOCUMENTS

PP28,257 P3 * 8/2017 Verwer ..... A01H 5/02
Plt./321

* cited by examiner

*Primary Examiner* — Susan McCormick Ewoldt
*Assistant Examiner* — Zachariah Allan Kay

(57) ABSTRACT

A new and distinct cultivar of *Dahlia* plant named 'LeeAnn's FD168C' is disclosed, characterized by unique tan-peach inflorescences on plants with a strong, upright growth habit. Flowers have a consistent quality throughout the growing season. Plants continue to produce new inflorescences in late season (less than 12 hours of daylight). Flowering stems have an above average strength with a firm blossom attachment. Inflorescences have strong postproduction quality. The new variety is a *Dahlia* typically produced for cut flower purposes, or garden or landscape.

2 Drawing Sheets

Figure 1:
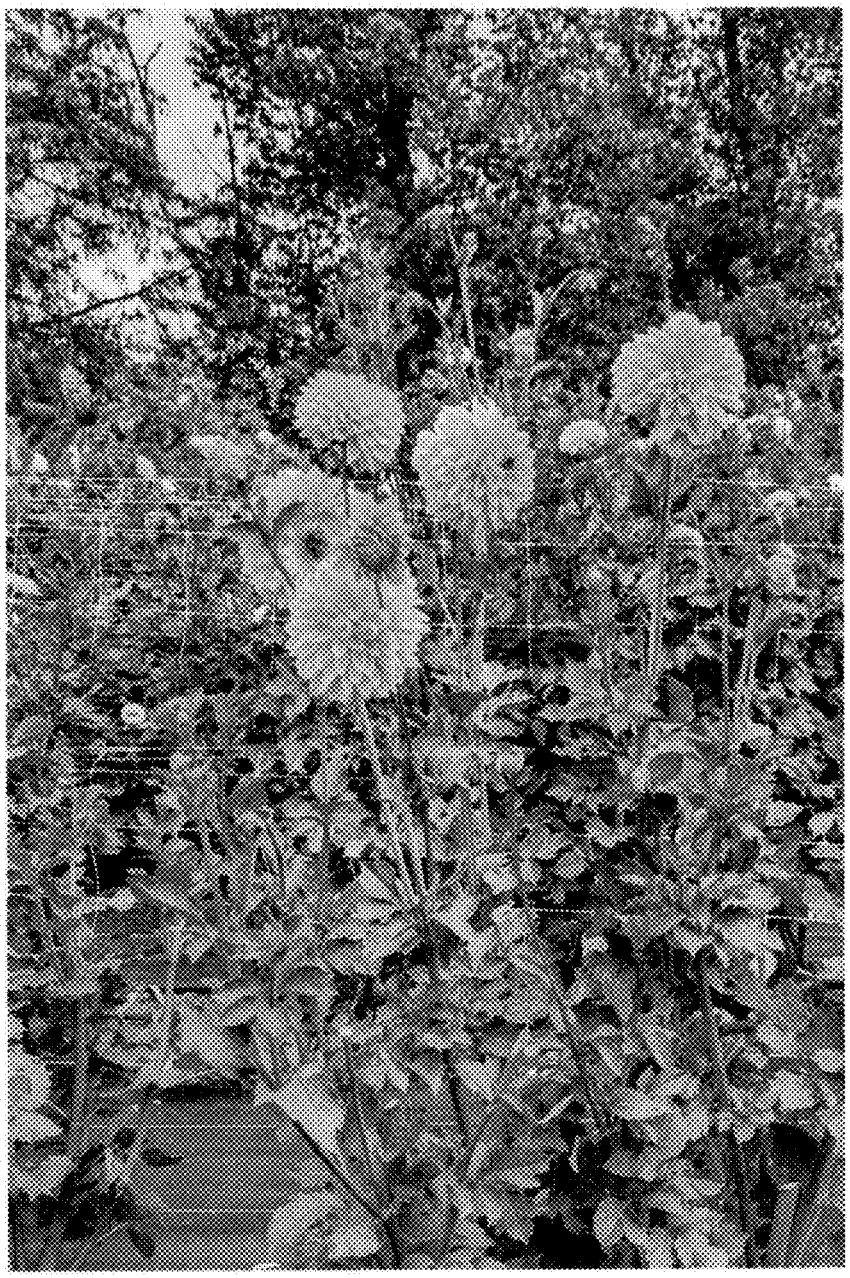

Latin name of the genus and species: *Dahlia hybrida.*
Variety denomination: 'LeeAnn's FD168D'.

BACKGROUND OF THE INVENTION

The new *Dahlia* cultivar is a product of a planned breeding program conducted by the inventor in Greencastle, Pennsylvania. The objective of the breeding program was to produce new *Dahlia* varieties with improved performance in open field conditions for the purpose of cut flower production suitable for transport and sale. The open pollination resulting in this new variety was made during the Fall of 2021.

The seed parent is an undistributed, unpatented, proprietary variety of *Dahlia* referred to as 'H276'. The pollen parent is unidentified. 'LeeAnn's FD168D' was intentionally selected in the Summer of 2022 based on the criteria of strong, upright growth, as well as free branching and flowers held above the leaf canopy. The new cultivar was selected in Greencastle, Pennsylvania.

Asexual reproduction of the new cultivar was first performed by root divisions by the inventor in Greencastle, Pennsylvania in the Spring of 2023 and has shown that the unique features of this cultivar are stable and reproduced true to type in successive generations.

SUMMARY OF THE INVENTION

The cultivar 'LeeAnn's FD168D' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's FD168D' These characteristics in combination distinguish 'LeeAnn's FD168D' as a new and distinct *Dahlia* cultivar:

1. Strong postproduction inflorescence quality as a cut flower. Petals remain hydrated without wilting or browning for 8 days.
2. Early blooming; flowering begins with 70 to 75 days.
3. Consistency of inflorescence quality throughout the growing season. Petal count is maintained even as daylight hours diminish.
4. Consistency of inflorescence color throughout the growing season.
5. Plants continue to produce new inflorescences in late season (less than 12 hours of daylight).
6. Unique tan-peach inflorescence with a darker, pinker center.

PARENT COMPARISON

Plants of the new cultivar 'LeeAnn's FD168D' are similar to plants of the seed parent, in some horticultural characteristics, however, plants of the new cultivar 'LeeAnn's FD168D' differ in the following;

1 'H276' is considered a waterlily form according the American *Dahlia* Society standards while 'LeeAnne's FD168D' is a formal decorative by the same standard.
2. The new cultivar produces more ray florets per inflorescence than the seed parent.
3. Plant height of the seed parent is 65 inches' plant height of 'LeeAnn's FD168D' is about 53 inches.

4. The seed parent has been observed to produce seed; the new cultivar has not been observed to produce seed since its selection.

The pollen parent cannot be identified with certainty.

COMMERCIAL COMPARISON

Plants of the new cultivar 'LeeAnn's FD168D' are comparable to the variety *Dahlia* 'Apricot Desire', unpatented. The two *Dahlia* varieties are similar in most horticultural characteristics; however, the new variety 'LeeAnn's FD168D' differs in the following:

1. 'LeeAnn's FD168D' plant height is around 53 inches; plant height of 'Apricot Desire' is around 40 inches.
2. 'Apricot Desire' has dark purple peduncles; 'LeeAnn's FD168D' has Yellow-green peduncles tinged reddish brown on the upper surface.
3. 'Apricot Desire' is considered a waterlily form according the American *Dahlia* Society standards while 'LeeAnne's FD168D' is a formal decorative by the same standard.

Plants of the new cultivar 'LeeAnn's FD168D' are comparable to the variety *Dahlia* 'Yvonne', unpatented. The two *Dahlia* varieties are similar in most horticultural characteristics; however, the new variety 'LeeAnn's FD168D' differs in the following:

1. 'LeeAnn's FD168D' plant height is around 53 inches; plant height of 'Yvonne' is around 42 to 45 inches.
2. 'Yvonne' has very dark purple peduncles; 'LeeAnn's FD168D' has Yellow-green peduncles tinged reddish brown on the upper surface.
3. 'LeeAnne's FD168D' produces more ray florets per inflorescence than 'Yvonne'.
4. Inflorescence color of 'Yvonne' will shift in color throughout the season ranging from light orange to coral pink; inflorescence color of the new cultivar is stable throughout the season.

BRIEF DESCRIPTION OF THE PHOTOGRAPHS

The accompanying photograph in FIG. 1 illustrates in full color typical cut flower stems from plants of 'LeeAnn's FD168D' grown outdoors, in the ground.

Figure 2:
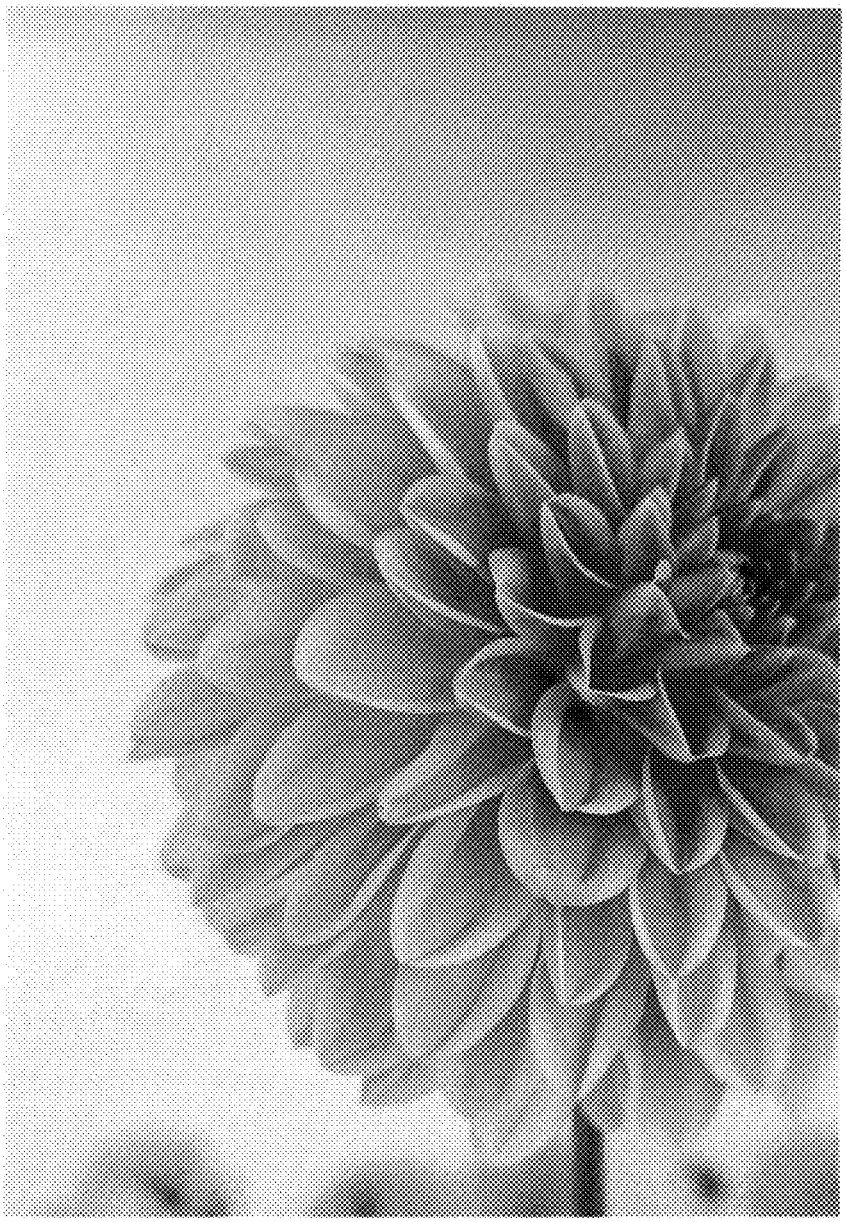

FIG. 2 illustrates a close-up of an inflorescence on plants grown outdoors. Age of the plants producing these inflorescences is approximately 115 days from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society R.H.S. Colour Chart 2015 except where general terms of ordinary dictionary significance are used. The following observations and measurements describe 'LeeAnn's FD168D' plants grown outdoors, in production cut flower rows in Greencastle, PA. The average growing season for outdoor cut flower production runs from May through mid-October or 24 weeks. The terminal bud is pinched off the *Dahlia* around 4-6 weeks of age. Temperatures ranged from Average 23° C. to 39° C. during the day and 7° C. to 23° C. at night. General light conditions are bright, normal sunlight. Botanical data was collected between May and September. Measurements and numerical values represent averages of typical plant types.

Botanical classification: *Dahlia* hybrida 'LeeAnn's FD168D'.

PROPAGATION

Time to initiate roots: During March 7 to 10 days at approximately 21° C.

Root description: Freely branching, fine rootlets with canescent hairs.

PLANT

Plant type: Herbaceous flowering perennial.

*Age of the plant described.*—Average 115 days.

*Plant height.*—53 inches.

*Plant spread.*—16.4 inches.

*Lateral branch length.*—46.9 inches.

*Lateral branch diameter base.*—10.94 mm.

*Lateral branch diameter apex.*—9.75 mm.

*$2^{nd}$ internode length.*—43.75 cm.

*Angle of inflorescence stem from lateral branch Average.*—26 deg.

*Branch strength.*—Exceptional, resistant to breakage from environmental factors.

*Branch texture.*—Glabrous and sulcate.

*Branch color.*—Near RHS Yellow-Green 146B upper and lower surfaces.

FOLIAGE

Leaf:

*Arrangement.*—Leaves opposite; leaves may be single, or composite with three, or five leaflets.

*Shape.*—Ovate.

*Apex.*—Acute.

*Base.*—Obtuse.

*Margin.*—Serrated.

*Aspect.*—Flat.

*Angle.*—Slightly upward.

*Texture.*—Upper surface: Glabrous. Lower surface: Glabrous.

*Leaf wings.*—Moderate.

*Length.*—Single leaves: Average 7.5 cm. Compound leaves with three leaflets: Average 12.4 cm. Compound leaves with five leaflets: average 15.4 cm.

*Width.*—Single leaves: average 5.2 cm. Compound leaves with three leaflets: average 10.34 cm. Compound leaves with five leaflets: average 13.88 cm.

*Leaf color.*—Developing foliage: Upper Surface: Green N137B. Lower Surface: Yellow-Green 147B. Fully developed: Upper Surface: Yellow-Green 147A. Lower Surface: Yellow-Green 147B.

*Venation pattern.*—Pinnate. Color: Upper surface: Yellow-Green 148B. Lower surface: Yellow-Green 148A.

*Petiole length.*—Single leaves: Average 3.1 mm. Compound leaves with three leaflets: Average 13.7 mm. Compound leaves with five leaflets: Average 32.4 mm.

*Petiole diameter.*—Single leaves: Average 3.4 mm. Compound leaves with three leaflets: Average 2.6 mm. Compound leaves with five leaflets: Average 3.4 mm.

*Petiole texture*.—Upper and lower surfaces: Smooth and glabrous.

*Petiole color*.—Upper Surface: Yellow-Green 145C tinged 177A. Lower surface: Yellow-Green 145C.

Stipule: Not present.

FLOWER

Days to flowering from rooted cutting: Plants begin to bloom around 70 to 75 days after planting; continuously blooming until the season ending frost in Pennsylvania while maintaining good ray floret count and inflorescence form.

Natural flowering season: During frost free days and nights beginning late April/early May through end of September or early October.

Inflorescence and flower type and habit: Formal decorative form *Dahlia* with both ray and disc florets present. Positioned above or slightly above the leaf canopy.

Rate of flower opening: 7 to 8 days from bud to fully opened flower.

Flower longevity on plant: Inflorescence maintains good substance (attractive color with good moisture content) on the plant for an average of 14 to 15 days.

Flower longevity as a cut flower: For Average 8 days as a cut flower (fresh water at room temperature).

Flowers per plant: Average 10 at one time.

Persistent or self-cleaning: Self Cleaning.

Inflorescence:

*Inflorescence position*.—Positioned above or slightly above the foliage on the strong peduncles (stalks) with upright to slightly outwardly face.

*Flower scent*.—Not fragrant.

Inflorescence bud:

*Shape*.—Oblate-spheroidal and flattened at the poles.

*Texture*.—Glabrous.

*Appearance*.—Semi-glossy.

*Color*.—Yellow-Green N144A.

*Height*.—13.3 mm.

*Diameter*.—17.2 mm.

Inflorescence size:

*Diameter*.—Average 9.4 cm.

*Height or depth*.—Average 5.7 cm.

*Receptacle diameter*.—1.6 cm.

Ray florets:

*Quantity*.—187. Arranged in an average of 13 whorls.

*Length*.—Average 42.6 mm.

*Width*.—Average 18.6 mm.

*Shape*.—Obovate. Attachment at the narrow end.

*Apex*.—Obtuse.

*Base*.—Attenuate.

*Margin*.—Entire.

*Aspect*.—Initially upright, developing to perpendicular and aging to reflexed.

*Margin roll*.—Flat.

*Aspect/petal curl*.—Weakly concave to flat.

*Texture*.—Upper surface — 3-keels. Smooth. Lower surface — 3-keels. Smooth.

*Color*.—When opening: Upper Surface: Principal Color 174B. Base 6A, lightly blending with 174B towards distal end. Lower Surface: Principal Color 171C, over ¾ distal end, nearly solid. Base 6A, blending with 171C at ¼ from base. Fully opened: Upper Surface: Distal half 168D flushed 5A. Base 5A, flushed 168D towards center. Lower Surface: Distal half 165D flushed 5A. Base 5A, flushed 165D towards center.

Disc florets:

*Disc diameter*.—Average 9 mm.

*Shape*.—Tubular.

*Apex*.—Dentate.

*Length*.—Average 7.1 mm.

*Diameter, base*.—Average 1.3 mm.

*Number of disc florets per inflorescence*.—Average 17.

*Immature color*.—Apex Yellow-Orange 17A, mid section Yellow-Orange 17A, base Yellow 2D.

Phyllaries:

*Quantity per inflorescence*.—Average 8.

*Length*.—Average 22.2 mm.

*Width*.—Average 9.3 mm.

*Arrangement*.—Whorl.

*Shape*.—Rhomboid.

*Apex*.—Acute.

*Base*.—Truncate.

*Margin*.—Entire.

*Texture*.—Upper surface: Smooth, glabrous, satiny appearance. Lower surface: Smooth, glabrous, satiny appearance.

*Color*.—Upper Surface Green 137C striped 137A. Lower Surface Green 137C striped 137A.

Peduncles:

*Strength of stem*.—Exceptionally strong. Peduncle strength is measured by assessing if any flexion occurs on harvested flower stems (peduncles) when the stem is given a brief, firm shake. Any stems which flex are considered average, stems which show damage are below average and stems which remain inflexible are above average and considered strong.

*Aspect*.—Upright.

*Texture*.—Smooth and glabrous.

*Color*.—Yellow-Green 146C tinged 177A.

*Average length*.—18.3 cm from base of inflorescence to closest leaf.

*Diameter at base*.—4.9 mm.

*Diameter at attachment*.—3.8 mm.

REPRODUCTIVE ORGANS

Stamen quantity per disc floret: 5, Connivant.

*Stamen attachment*.—Filament adnate to ventral surface of corolla.

*Stamen length*.—Average 8.4 mm.

*Anther shape*.—Connivant.

*Anther length*.—Average 4.5 mm.

*Anther color*.—Yellow-Orange 17A.

*Pollen amount*.—Moderate.

*Pollen color*.—Yellow-Orange 17A.

Pistil quantity per disc floret: 1.

*Pistil length*.—Average 16.5 mm.

*Stigma shape*.—Bifurcate.

*Stigma form*.—Plumose.

*Stigma length*.—Average 2.5 mm.

*Stigma width*.—Average 3.2 mm.

*Stigma color*.—Yellow 13A.

*Ovary position*.—Inferior.

*Ovary shape*.—Truncate.

*Ovary color*.—Green-Yellow 1D.
*Ovary length*.—Average 1.7 mm.
*Ovary width*.—Average 1.4 mm.

Ray florets: Ray florets closest to the disc florets will sometimes have both Androecium and Gynoecium.

Androecium when present:

Stamen quantity per ray floret: 5.

*Stamen attachment*.—Filament adnate to ventral surface of corolla.
*Stamen length*.—Average 4 mm.
*Anther shape*.—Connivant.
*Anther length*.—Average 1.9 mm.
*Anther color*.—Yellow-Orange 17A.
*Pollen amount*.—Moderate.
*Pollen color*.—Yellow-Orange 17A.

Pistil quantity per ray floret: On average 1 out of every 10 ray florets will have a pistil.

*Pistil length*.—Average 8 mm.
*Stigma shape*.—Bifurcate.
*Stigma length*.—Average 1.2 mm.
*Stigma width*.—Average 1.1 mm.
*Stigma color*.—Yellow 5C.
*Ovary position*.—Inferior.
*Ovary shape*.—Truncate.
*Ovary color*.—Green-Yellow 1D.
*Ovary length*.—Average 2.3 mm.
*Ovary width*.—Average 1.5 mm.

OTHER CHARACTERISTICS

Fruit/seed: Not observed to set seed to date.

Disease/pest resistance: Neither resistance nor susceptibility to normal diseases and pests of *Dahlia* has been observed.

Weather and climate performance: Plants of the new *Dahlia* have excellent tolerance to heat and high UV index, resisting wilting and fading in field grown conditions. Daylight length has minimal effects on bud and bloom production, maintaining cut flower output into late season light and weather conditions.

Temperature range: Generally considered a perennial in USDA Zones 8-11. Grown in any zone as an annual. Can be overwintered in Zone 6 and 7 with protective mulch. In zones 3-5 plants are considered annuals.

What is claimed is:

1. A new and distinct cultivar of *Dahlia* plant named 'LeeAnn's FD168D' as herein illustrated and described.

* * * * *